United States Patent
Lewandowski et al.

(10) Patent No.: US 6,939,713 B2
(45) Date of Patent: Sep. 6, 2005

(54) ASSAY AND METHOD FOR QUANTIFYING THE LEVELS OF STERYL ESTERS AND FREE STEROLS IN STARCH-CONTAINING FOOD PRODUCTS

(75) Inventors: Daniel J. Lewandowski, Bloomington, MN (US); David W. Plank, Taylors Falls, MN (US)

(73) Assignee: General Mills, Inc., Minneapolis, MN (US)

(*) Notice: Subject to any disclaimer, the term of this patent is extended or adjusted under 35 U.S.C. 154(b) by 223 days.

(21) Appl. No.: 10/172,390

(22) Filed: Jun. 14, 2002

(65) Prior Publication Data

US 2003/0232444 A1 Dec. 18, 2003

(51) Int. Cl.[7] .............................................. G01N 33/00
(52) U.S. Cl. ............................ 436/13; 436/71; 436/60; 436/174; 436/177
(58) Field of Search .............................. 436/13, 71, 60, 436/20, 174, 177

(56) References Cited

PUBLICATIONS

Tharanathan et al. Isolation and chemical characterization of lipopolysaccharides from four Mycoplana species (M. bullata, M. segnis, M. ramosa and M. dimorpha), Archives of Microbiology (1993), 159(5), 445–52, Abstract.*

Ahamed et al. "Lipopolysaccharide with 2,3–diamino–2, 3–dideoxyglucose containing lipid A in Rhodopseudomonas sulfoviridis" FEMS Microbiology Letters (1982), 14(1), 27–30, Abstract.*

Krekhova et al. Fractional determination of cholesterol esters in blood and tissues by thin–layer chromatography, Voprosy Meditsinskoi Khimii (1971), 17(1), 93–8, Abstract.*

Toivo et al. "Factors affecting sample preparation in the GC determination of plant sterols in whole wheat flour", Food Chemistr 2000, v. 68, pp. 239–245.*

Abidi "Chromatographic analysis of plant sterols in foods and vegetable oils", J. Chromatogr. A, 2001, v. 935, pp. 173–201.*

Gordon et al. "Development of steryl ester analysis for the detection of admixtures of vegetable oils", J. Am. Oil Chem., 1997, v. 74, No. 5, pp. 505–510.*

Rivabene et al. "Redox–dependent modulation of lipid synthesis induced by oleic acid in the human intestinal epithelial cell LineCaco–2", Exp. Biol. Med., 2001, v. 226, pp. 191–198.*

* cited by examiner

Primary Examiner—Yelena G. Gakh
(74) Attorney, Agent, or Firm—Arlene L. Hornilla; Dale A. Bjorkman; Douglas J. Taylor

(57) ABSTRACT

The present invention relates to an assay for determining the levels of sterols, stanols, steryl esters, fatty acid derivatives and combinations thereof in a starch-containing food product. The assay is particularly useful in supporting product health and/or nutritional claims in manufacturing products intended for human or animal consumption. The present invention describes a method for extracting sterols related compounds and uses as an internal standard a steryl ester, preferably cholesterol oleate. By using the present extraction technique the process enables the recovery of substantially all of the sterol related compound in the sample.

12 Claims, 2 Drawing Sheets

Effect of Amylopectin on Sterol Determinations

ASSAY AND METHOD FOR QUANTIFYING THE LEVELS OF STERYL ESTERS AND FREE STEROLS IN STARCH-CONTAINING FOOD PRODUCTS

CROSS-REFERENCES TO RELATED APPLICATIONS

None.

BACKGROUND OF THE INVENTION

Manufacturers of consumer goods, specifically, manufacturers of food products annually devote a substantial amount of time, effort and resources to improving the products they offer. These improvements can take the form of improved taste or texture, reduced calories or fat content and the like. More recently, and as the population matures, food companies are looking more and more into food products, food components or ingredients that deliver a particular health or nutritional benefit. That is, food products that may assist the consumer in living a healthier life in that the food product aids in reducing high cholesterol levels, mitigating the risk of heart diseases, diminishing the risk of some cancers and many other illnesses and diseases, which become more prevalent as society ages or dietary patterns are modified to meet the changing lifestyles of today's population.

One health claim that has received a lot of interest lately is the effect of using sterols/stanol, steryl esters and other fatty acid derivatives and combinations thereof to reduce unhealthy or high cholesterol levels. In this regard, a number of internationally known food manufacturers have successfully manufactured and marketed starch-containing food products that have certain levels of sterols and steryl esters in order to deliver a product that provides this health benefit. Such starch-containing food products include ready to eat (RTE) cereals, dough based products, RTE meals and the like.

It is well known that cholesterol in humans comes from primarily two sources, the body's own production of cholesterol (endogenous) and dietary cholesterol (exogenous). Typically, the average person consumes between 350–400 milligrams of cholesterol daily, while the recommended intake is around 300 milligrams. Increased dietary cholesterol consumption, especially in conjunction with a diet high in saturated fat intake, can result in elevated serum cholesterol. Elevated serum cholesterol is a well-established risk factor for heart disease and therefore there is a need to mitigate the undesired effects of cholesterol accumulation. High cholesterol levels are generally considered to be those total cholesterol levels at 200 milligrams per deciliter and above or LDL cholesterol levels at 130 milligrams per deciliter and above.

Lipoproteins contain specific proteins and varying amounts of cholesterol, triglycerides and phospholipids. There are three major classes of lipoproteins and they include very low density lipoproteins ("VLDL"), low density lipoproteins ("LDL") and high density lipoproteins ("HDL"). The LDLs are believed to carry about 60–70% of the serum cholesterol present in an average adult. The HDLs carry around 20–30% of serum cholesterol with the VLDL having around 1–10% of the cholesterol in the serum. To calculate the level of non-HDL cholesterol present (find the level of LDL or VLDL levels), which indicates risk, the HDL is subtracted from the total cholesterol value. By lowering the total system LDL cholesterol level, it is believed that certain health risks, such as coronary disease and possibly some cancers, that are typically associated with high cholesterol levels, can be reduced.

Numerous studies relating to modifying the intestinal metabolism of lipids have been done to illustrate that such effects can reduce a high cholesterol level. This may be done by hampering the absorption of triglycerides, cholesterol or bile acids. It is believed that certain plant sterols, steryl esters, stanols fatty acid derivatives and combinations thereof lower serum cholesterol levels by reducing the absorption of dietary cholesterol and/or bile acids from the intestines.

Sterols occur in natural fats and oils, particularly in vegetable oils. Unsaturated vegetable oils and non-animal fat oils, such as soybean oil, wheat germ oil, cottonseed oil, safflower oil, peanut oil, rice oil, canola oil and the like are well known sources of β-sitosterol, stigmasterol, ergosterol and campesterol as well as various other materials such as higher aliphatic alcohols. Tall oil is also a significant source of β-sitosterol and campesterol.

Stanols (β-sitostanol, campestanol, stigmastanol and fatty acid derivatives thereof) are the 5 alpha saturated derivatives of plant sterols and may be derived from similar sources set forth above.

Natural plant sterols are similar structurally to cholesterol except in the arrangement of the basic side chains. Absorption of plant sterols in the intestines is believed to be minimal at best and sterols/steroids are generally excreted in the stool. Thus, the levels of plant sterols in the serum are relatively low since they are not absorbed by the body and are relatively quickly excreted. Where the amount of sterols is increased in an effort to obtain greater beneficial or health effects, the sterols still do not increase significantly in amount in the blood serum as the absorption capability, however limited it may be, is quickly exceeded. Hence, the interest in including sterol related or containing compounds in food products, food ingredients and food components (the presumed health benefit stated above) is directly related to the manufacturer's interest in sterol inclusion into such products.

In manufacturing products that contain certain health claims, such as a RTE cereal, i.e. TOTAL® or CHEERIOS® available from General Mills, Inc. of Minneapolis, Minn., it is important that the product not only be able to support or substantiate the health claim for regulatory reasons but also that the product must actually contain the amount of the effective ingredient stated in the nutritional information provided with the package. One of the problems associated with making foods having sterol related or containing compounds is determining or verifying the actual level of sterol related or containing compounds in the end product to be consumed.

Thus, there is a need for food manufacturers to be able to accurately calculate or quantify the amount of the sterols and steryl esters in a food product so that the proper amount is delivered in each of the suggested serving or portion sizes in order that the claims of the food product are supported by the contents.

Heretofore, a number of methods using a variety of internal standards have been developed to attempt to calculate the amount of sterol related or containing compounds in the food product. However, these methods while possibly being relatively quick and inexpensive to use can in fact be detrimental to both the manufacturer from both a cost and a regulatory standpoint as well as the consumer of the product from a health related aspect.

With respect to prior methodologies employed by the food product manufacturer, readings related to determining the level of sterol based or containing compounds provided by these methods often resulted in a reading that was substantially lower than the actual amount of sterols or steryl esters that may have been added to the food products during the manufacturing process, that is, that amount added to provide or obtain the health or nutritional benefit. Often, it was found that readouts from these prior test methods would be from twenty-five to fifty percent (25–50%) lower than the actual amount of the ingredient or component that was added. Such readings would then result in the manufacturer adding even more of the ingredient or component to insure that the food product would be supported by the claims and nutritional information provided with the package, that is in the present example, to insure that enough of the sterol based compound is present. While this is a simple solution, it has significant economic disadvantages in that sterol related compounds are relatively expensive ingredients when compared on a relative weight basis with other ingredients present in the product, i.e. the grain (wheat, oat, barley), sugar, macro and micro nutrients, etc. There are also other significant disadvantages to having excessive amounts of sterol containing compounds in the food products. As used herein, the term "food products" includes food components (such as dough, flakes), food intermediates (a transitional step used in making a product or component) and a food ingredient. Where the term "food product" is used in connection with a manufacturer or manufacturing, the term is intended to imply an entity, which makes, fabricates, processes or produces food products as defined above.

It is important to insure that the right amount of the ingredient is available in each serving or portion size, not only from a manufacturing but also a regulatory standpoint. From a manufacturing point of view, cost of manufacture is a significant factor in determining profit levels. However, from a regulatory standpoint, providing an amount of sterols and steryl esters beyond an acceptable threshold can be detrimental to the health of the consumer. As such, there is a maximum amount of the ingredient that cannot be exceeded in order to qualify for the generally recognized as safe ("GRAS") status of such sterol related compounds. As used herein, the term sterol related or containing compound refers to such compounds as β-sitosterol, stigmasterol, ergosterol, campesterol, stanols β-sitostanol, campestanol, stigmastanol and fatty acid derivatives thereof.

It is believed that the prior testing methods, which used an internal standard of cholestane, produced unacceptable results in part due to the fact that cholestane did not sufficiently chemically simulate the compounds that were being assayed to compensate for degradation or matrix binding. The problem of getting an accurate reading using current methods is that the steryl esters and sterols are bound by the starch (most probably amylopectin) during the cooking process, which is inherent in most food product manufacturing steps. Using such internal standards prior test methods were ineffectual in releasing the starch bound sterols and steryl esters resulting in readings being off by as much as fifty percent (50%) from the known amount of ingredient or component that was added to the food product or food component initially.

What is needed therefore is an accurate method for determining or quantifying the level of the sterol related or containing compounds in a particular starch containing or consumer food product or component which has a health claim or benefit associated with it so as to insure compliance with self-affirmed GRAS status as well as to maintain manufacturing economies in scale with target projections.

SUMMARY OF THE PRESENT INVENTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

In a presently preferred embodiment of the present invention, the invention comprises an extraction method to be able to quantify the amount of sterol based compounds in starch-containing food product, which includes the steps of providing an amount of a steryl ester, preferably cholesterol oleate, and then initially hydrating a polysaccharide matrix of a starch-containing food product. Then mixing the matrix with an organic solvent. The organic phase is separated from an aqueous phased which was created by the mixing process. The organic phase is then subject to a drying step in order that the level or amount of sterol based compounds in the starch containing food product can be determined.

A still further preferred embodiment of the present invention sets forth an assay for determining quantities of sterols, stanols, steryl esters, fatty acid derivatives and combinations thereof in a cereal based product using a steryl ester as an internal standard. Preferably, the steryl ester is cholesteryl oleate.

A additional preferred embodiment of the present invention relates to an assay for determining quantities of sterols, stanols, steryl esters, fatty acid derivatives and combinations thereof in which more than 90%, preferably closer to 100%, of the sterols, stanols, steryl esters, fatty acid derivatives and combinations thereof are recovered for quantification.

Another embodiment of the present invention includes a method for substantiating the presence or absence of sterol based compositions that are found in a consumer food product. This method comprises the steps of, initially obtaining a consumer food product and then separating the consumer food product into certain fractions. Once the fractions are separated, at least one of the fractions are hydrated. Next, an organic solvent is added to the hydrated fraction. This hydration creates an organic phase which is sequestered from the organic phase of the hydrated fraction. Using an internal standard of a sterol related compound the amount of sterol based compounds in the consumer food product is determined. Once the amount of sterol based compound is determined that result is communicated to deliver a particular health message related to the presence of the sterol based compound.

A still further embodiment of the present invention relates to a method of reporting a health benefit of a consumer food product. This method comprises the steps of initially manufacturing a food product that is intended for human consumption. (Although only human consumption is referenced herein, this embodiment as well as the other embodiments provided in this application may include food products that are intended for animal consumption as well.) In order to determine the presence or absence of a sterol related compound in the food product, an internal standard of a sterol related compound is provided as a reference. The food product is then hydrated to create a matrix through the addition of an organic solvent. An organic phase of the matrix is separated and analyzed to obtain a level of sterol related compounds found in the hydrated food product. Finally, once the amount of sterol related compounds in the food product is known, a health benefit of the food product containing sterol related compounds is advertised to potential consumers of the health product.

Publications, patents and patent applications are referred to throughout this disclosure. All references cited herein are hereby incorporated by reference. All percentages and ratios are calculated by weight unless otherwise indicated. All percentages and ratios are calculated based on the total composition unless otherwise stated.

These, as well as other objects and advantages of this invention, will be more completely understood and appreciated by referring to the following more detailed description of the presently preferred exemplary embodiments of the invention in conjunction with the accompanying drawings.

BRIEF DESCRIPTION OF THE DRAWINGS

These, as well as other objects and advantages of this invention, will be more completely understood and appreciated by referring to the following more detailed description of the presently preferred exemplary embodiments of the invention in conjunction with the accompanying drawings, of which.

DETAILED DESCRIPTION OF THE INVENTION

The present invention is now illustrated in greater detail by way of the following examples, but it should be understood that the present invention is not to be construed as being limited thereto.

In the preferred embodiment, a starch containing food product, such as an RTE cereal is prepared in a conventional manner. This exemplary RTE cereal is in the form of flakes that are created by preparing a cooked cereal dough through known methods and then forming the cooked cereal dough into pellets that have a desired moisture content. The pellets are then formed into wet flakes by passing the pellets through chilled roller and then subsequently toasting or heating the wet cereal flakes. The toasting causes a final drying of the wet flakes, resulting in slightly expanded and crisp RTE cereal flakes. The flakes are then screened for size uniformity. The final flake cereal attributes of appearance, flavor, texture, inter alia, are all affected by the selection and practice of the steps employed in their methods of preparation. For example, to provide flake cereals having a desired appearance feature of grain bits appearing on the flakes, one approach is to topically apply the grain bits onto the surface of the flake as part of a coating that is applied after toasting.

Figure 2:
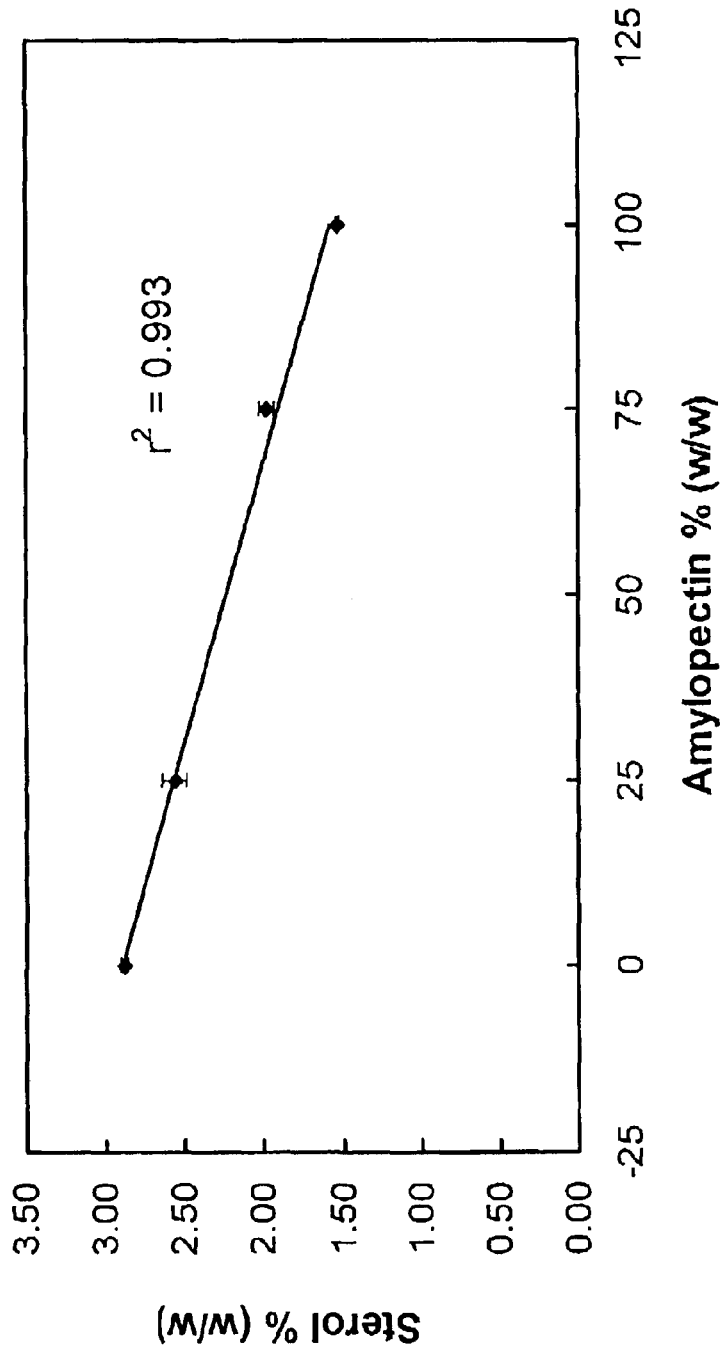
FIG. 2 is a graph showing the correlation of the level of sterol determined by the prior method to the amylopectin content of cooked doughs.

In the following example, the assay is based on using an internal standard of cholestryl oleate instead of cholestane, which has been perceived as producing unacceptable results as typified in the graph illustrated in FIG. 2. As set forth previously, it is believed that cholestane did not sufficiently, chemically simulate the compounds that were being assayed to compensate for degradation or matrix binding which further exacerbates the problem of getting an accurate reading in that the steryl esters, stanols and sterols are bound by the starch (most probably amylopectin) during the cooking process. By using the following process substantially all, that is greater than 90%, but typically closer to 100% of the sterol related compounds that is added to the sample product is recovered.

Example A Extraction of Steryl Esters/Sterols/Stanos from Cooked Cereal Products:
1. Add Cholesterol Oleate (0.1 mg) to a clean 20 ml glass scintillation vial with phenolic foil lined cap ("Vial").
2. Weigh out 0.1000 gram of sample into the Vial.
3. Add 2.0 ml of Solution 0.1 M Acetic Acid with 0.7% (w/v) KCl to hydrate the polysaccharide matrix of the sample.
4. Heat Sample at 95° C. for 30 minutes.
5. Cool sample to room temperature.
6. Add 10 ml of HPLC grade chloroform to the sample. Alternatively, add 10 ml of 2:1 Chloroform:MeOH. Seal cap tightly. Incubate at 37° C. for 12–16 hours with constant shaking at 250 rpm.
7. Focus organic and aqueous phase by centrifuging for 10 min at 5000 rpm separating the organic phase from the aqueous phase.
8. Withdraw bottom layer (chloroform or chloroform:MeOH) from the vial with a 10 ml gas tight syringe. Avoiding the aqueous layer during the draw. Transfer to a clean flask and dry down.
9. Transesterify using Alltech MethPrep II (Alltech Associates, Inc., Deerfield, Ill. 60015, USA) or sodium methoxide. Alternatively, saponify samples.
10. Silanate samples and inject on to GC with FID detector (Hewlett Packard 5890 Gas Chromatograph; Agilent Technologies Palo Alto, Calif. 94303 USA ) or Mass Spec detector(Hewlett Packard Model 5970 MSD; Agilent Technologies Palo Alto, Calif. 94303 USA) to quantify or determine the amount or level of sterol related compounds that are found in sample.

The following example uses enzymes to digest the carbohydrate and protein matrix and is thought to obtain substantially all, that is greater than 90%, but typically closer to 100% of the sterol/stanol/steryl ester that is added to the sample product is recovered.

Example B Extraction of Steryl Esters/sterols/stanols from Cooked Cereal Products
1. Add Cholesteryl Oleate (0.1 mg) to a clean 20 ml glass scintillation vial with phenolic foil lined cap (Vial).
2. Weigh out 0.1000 gram of sample into Vial.
3. Add 2.0 ml of Solution A-2 to hydrate the polysaccharide matrix of the sample (see below).
4. Heat Sample at 95° C. for 30 minutes.
5. Cool Sample to 50° C. then add 400 ul of Enzyme Solution 1 (see below). Incubate at 50° C. for 3 hours. Vortex occasionally.
6. Add 100 ul of Enzyme Solution 2 (see below). Incubate at 50° C. for 1 hour. Vortex occasionally.
7. Add 20 ul of 50% Acetic acid (Final Conc. ~0.1 M Acetic Acid).
8. Add 10 ml of HPLC grade chloroform. Seal cap tightly. Incubate at 37° C. for 12–16 hours with constant shaking at 250 rpm.
9. Focus organic and aqueous phase by centrifuging for 10 min at 5000 rpm separating the organic phase from the solution.
10. Withdraw bottom layer (chloroform) from the vial with a 10 ml gas tight syringe. Be sure not to draw any of the aqueous layer into the syringe. Transfer to a clean flask and dry down.
11. Transesterify using Alltech MethPrep II (Alltech Associates, Inc., Deerfield, Ill. 60015, USA) or sodium methoxide. Alternatively, saponify samples to determine the amount or level of sterol related compounds in the food product sample.
12. Silanate samples and inject on to GC with FID(Hewlett Packard 5890 Gas Chromatograph; Agilent Technologies Palo Alto, Calif. 94303 USA) detector or Mass Spec detector.

Solution A2:
20 mM $KH_2PO_4$, pH 7.2

150 mM NaCl 50 mM KCl

Enzyme Solution 1: (make just prior to use)

2 grams α-Amylase 4 ml Amyloglucosidase (volume to 500 ml with Solution A2—above)

Enyme Solution 2: (make just prior to use)

1 gram Papain 0.6 grams Dithiothreitol (19.5 mM)

volume to 200 ml with Solution A2 (above)

Figure 1:
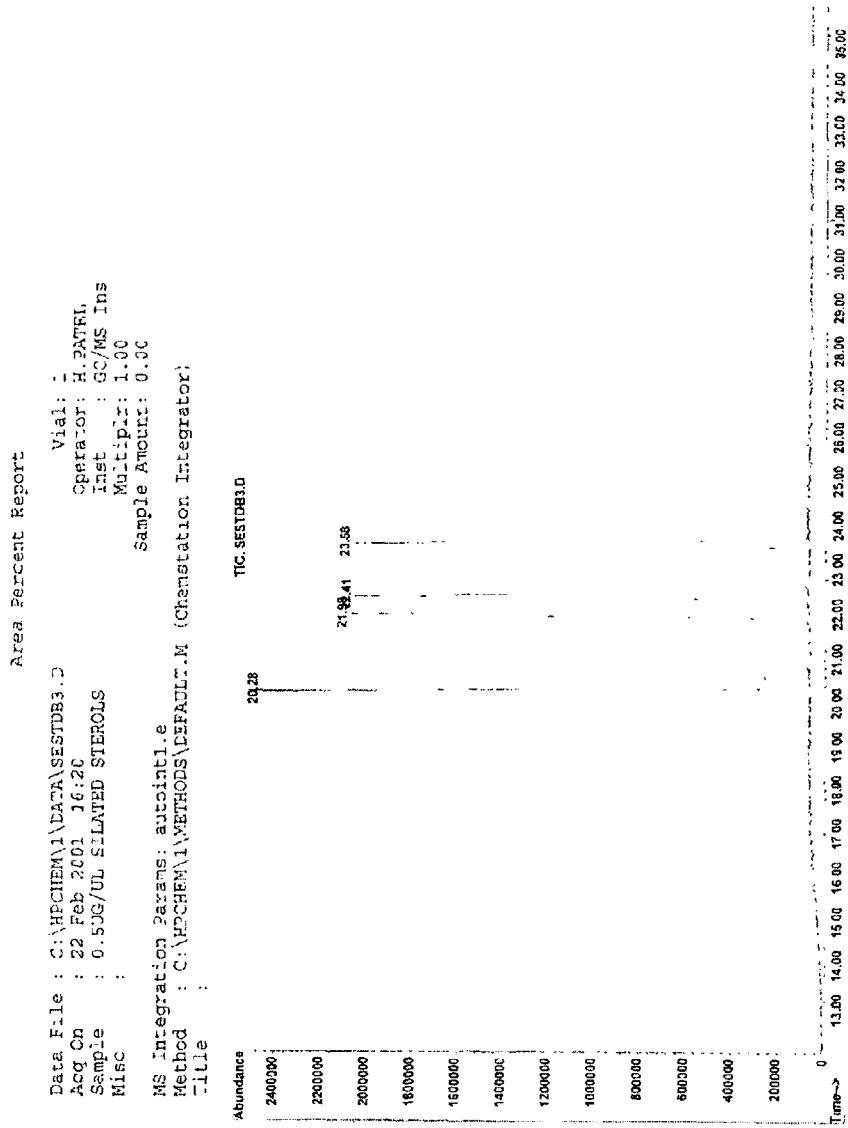
FIG. 1 is a gas chromatograph illustrating sterol standards.

In order to determine the amount of sterols, stanols, steryl esters, fatty acid derivatives or combinations thereof which have been recovered by using one of the aforementioned examples, the sample is subjected to gas chromatography. FIG. 1, illustrates the standard peaks for sterols.

Cooked starch-containing dough samples with increasing concentrations of amylopectin and fixed amounts of added steryl esters were assayed using one of the above referenced processes but having cholestane as the internal standard. FIG. 2, illustrates that the assay using the internal standard of cholestane underestimates the amount of steryl ester in a well correlated manner ($r^2=0.993$) to the total amount of amylopectin present in the sample.

The following table lists the results of exemplary RTE cereal samples, which were tested after using the process described in the above referenced examples. Example A lists values obtained using the process contained herein whereas Example B lists values obtained using cholestane as an internal standard over which the method of the present invention is an improvement over.

TABLE 1

Sterol Determinations

| Sample Name | Sterol Target | Example A | Example B |
|---|---|---|---|
| Batch Flake | 2.00 | 2.05 ± 0.16 | 1.49 ± 0.10 |
| Clinical James Flake | 4.10 | 3.93 ± 0.2 | 2.87 ± 0.07 |
| James Flake 1715 | 3.00 | 3.04 ± 0.12 | 1.75 ± 0.23 |
| James Flake 1915 | 3.20 | 3.14 ± 0.05 | 1.92 ± 0.14 |
| HSE Flake 11001 | 2.50 | 2.53 ± 0.01 | 1.56 ± 0.09 |
| LSE Flake 12501 | 2.00 | 2.09 ± 0.05 | 0.87 ± 0.18 |

In conducting a comparison of standard steryl esters processed in the absence of a cereal matrix by the process set forth above using either an internal standard of cholesteryl oleate or cholestane the following results were reported in Table 2. These results demonstrate that the cholestane is being recovered in higher yield relative to the silated sterol standards resulting in a lower value for the measured sterols that use the cholestane internal standard. Unlike cholesteryl oleate, cholestane is unesterified during the initial extraction steps and will therefore have different affinity for compounds and/or matrices that may irreversibily bind steryl esters. Following the saponification or transesterification, cholesteryl oleate and the other steryl esters will yield a free sterol with a hydroxyl group at the 3 position of the sterol ring. This hydroxyl group can cause the free sterol to irreversibly bind to glassware being used in the assay. Cholestane lacks the hydroxyl at the 3 position. This may also explain its higher yield relative to the measured sterols.

TABLE 2

Sterol Determinations

| Sample Name | Sterol Target | Example B |
|---|---|---|
| Sterol Stds (cholestane) | 100.00 | 89.96 ± 0.64 |
| Sterol Stds (cholesteryl oleate) | 100.00 | 98.41 ± 1.58 |

In table 3, the first column represents the sample being tested. In this table, in addition to RTE cereals (batch flake and clinical test), a dough, which may be used for breads, muffins and other baked goods is also tested. The second column represent the sterol related compound based target, the third column using the process described herein and the fourth column represents the percent difference of second and third columns.

TABLE 3

Sterol Determinations

| Sample Name | Sterol Target | Test A | % Difference |
|---|---|---|---|
| Brabender Var 1 | 2.32 | 2.38 ± 0.03 | 2.6 |
| Brabender Var 2 | 3.08 | 3.08 ± 0.14 | 2.0 |
| Brabender Var 3 | 3.71 | 3.98 ± 0.21 | 7.2 |
| Barbender Var 4 | 4.46 | 4.50 ± 0.06 | 0.8 |
| James Flake | 2.94 | 3.09 ± 0.16 | 5.1 |

It is believed that each of the foregoing tables illustrate the significant improvement of recovery of sterol related compounds from starch-containing food products or food components, when compared with previous methods that have used cholestane as the internal standard have not hydrated the starch matrix prior to extraction.

As can be seen from the tables, by using the novel assay of the present invention significantly more of the sterol related compounds are recovered when compared with previous or prior art methods.

In practicing the method embodiments of the present invention applicants the resultant reports are then provided in a manner that enables the communication or advertising of the benefit of having various levels or amounts of sterol related compounds in the food products. This advertising or communication can take any number of forms including the printing of the benefit of sterol compounds for the reduction of cholesterol levels on the packaging of the food product, through the use of audiovisual devices such as television, computer enabled devices and printed indicia such as newspapers, magazines, newsletters and the like.

The methods of the present invention as well as the assay itself is useful in the determination of the levels of sterol related compounds in ready to eat food products. Ready to eat food products (RTE) for the purposes of this invention include baked goods, salted snacks, specialty snacks and confectionary snacks as well as dairy products. Many of the aforementioned products can be dough based products, that is a dough is created, usually from a mixture of flour, water and other ingredients to necessary for the finished product.

It will thus be seen according to the present invention a highly advantageous test methodology has been provided. While the invention has been described in connection with what is presently considered to be the most practical and preferred embodiment, it will be apparent to those of ordinary skill in the art that the invention is not to be limited to the disclosed embodiment, that many modifications and equivalent arrangements may be made thereof within the scope of the invention, which scope is to be accorded the broadest interpretation of the appended claims so as to encompass all equivalent processes, methodologies and assays.

What is claimed is:

1. An assay for determining quantities of sterol related compounds in a starch-containing food product comprising:
   providing an amount of a steryl ester as an internal standard;
   adding said internal standard to a food product containing a polysaccharide matrix;
   hydrating a said polysaccharide matrix of said food product;
   mixing said hydrated polysaccharide matrix with an organic solvent;
   de-esterifying the steryl esters in the organic solvent;
   quantifying at least a level of either steryl esters and free sterols in said food product by a method using said steryl ester as an internal standard.

2. The assay of claim 1, wherein the organic solvent is chloroform.

3. The assay of claim 1, wherein the organic solvent is a mixture of chloroform and methanol.

4. The assay of claim 3, wherein the mixture of chloroform and methanol is provided in a ratio of 2 to 1.

5. The assay of claim 1, wherein the steryl ester is cholesteryl oleate.

6. The assay for determining quantities of sterol related compounds in a starch-containing food product as recited in claim 1, wherein the steryl ester is cholesteryl oleate.

7. The assay as recited in claim 1 wherein the assay is used to determine levels of sterols, stanols, steryl esters, fatty acid derivatives and combinations thereof in a cereal based product.

8. The assay as recited in claim 1 wherein the starch-containing food product is a ready to eat cereal.

9. The assay as recited in claim 1 wherein the starch-containing food product is a dough.

10. The assay as recited in claim 1 wherein at least 90% of the sterols, stanols, steryl esters, fatty acid derivatives and combinations thereof is recovered for quantification.

11. The assay of claim 1 further comprising
    communicating the amount of sterol based compounds found in said consumer based food products.

12. The assay of claim 1, wherein the step of de-esterifying the steryl esters comprises separating the organic phase from an aqueous phased created by said mixing of said matrix with said organic solvent; and
    drying said organic phase.

* * * * *

UNITED STATES PATENT AND TRADEMARK OFFICE
CERTIFICATE OF CORRECTION

PATENT NO. : 6,939,713 B2
DATED : September 6, 2005
INVENTOR(S) : Daniel J. Lewandowski, David W. Plank and Jonathan W. DeVries It is certified that error appears in the above-identified patent and that said Letters Patent is hereby corrected as shown below:

<u>Title page,</u>
Item [75], Inventors, delete current Inventor and insert -- Daniel J. Lewandowski, Bloomington, MN (US); David W. Plank, Taylors Falls, MN (US); Jonathan W. DeVries, Coon Rapids, MN (US) --.

Signed and Sealed this

Seventeenth Day of January, 2006

JON W. DUDAS
*Director of the United States Patent and Trademark Office*